(12) United States Patent
Cao et al.

(10) Patent No.: US 11,304,935 B2
(45) Date of Patent: Apr. 19, 2022

(54) USE OF I-BRD9 OR DERIVATIVES THEREOF IN PREPARING ANTI-EPILEPTIC DRUGS

(71) Applicant: UNIVERSITY OF SOUTH CHINA, Hunan (CN)

(72) Inventors: Wenyu Cao, Hunan (CN); Yang Xu, Hunan (CN); Dan Luo, Hunan (CN); Wei Wan, Hunan (CN); Jie He, Hunan (CN); Xiaolin Zhong, Hunan (CN); Xi Chen, Hunan (CN); Zhenghai Liu, Hunan (CN); Jiayu Zeng, Hunan (CN); Zhen Wang, Hunan (CN); Hui Yang, Hunan (CN); Lei Niu, Hunan (CN); Shishi Luo, Hunan (CN)

(73) Assignee: UNIVERSITY OF SOUTH CHINA, Hunan (CN)

( * ) Notice: Subject to any disclaimer, the term of this patent is extended or adjusted under 35 U.S.C. 154(b) by 4 days.

(21) Appl. No.: 16/961,267

(22) PCT Filed: Sep. 25, 2019

(86) PCT No.: PCT/CN2019/107775
§ 371 (c)(1),
(2) Date: Jul. 10, 2020

(87) PCT Pub. No.: WO2020/125118
PCT Pub. Date: Jun. 25, 2020

(65) Prior Publication Data
US 2021/0059994 A1 Mar. 4, 2021

(30) Foreign Application Priority Data
Dec. 18, 2018 (CN) .......................... 201811548181.6

(51) Int. Cl.
| | | |
|---|---|---|
| *A61K 31/4365* | (2006.01) | |
| *A61P 25/08* | (2006.01) | |
| *A61K 9/00* | (2006.01) | |
| *A61K 9/14* | (2006.01) | |
| *A61K 45/06* | (2006.01) | |

(52) U.S. Cl.
CPC ........ *A61K 31/4365* (2013.01); *A61K 9/0019* (2013.01); *A61K 9/14* (2013.01); *A61K 45/06* (2013.01); *A61P 25/08* (2018.01)

(58) Field of Classification Search
CPC .... A61K 31/4365; A61K 9/0019; A61K 9/14; A61K 45/06; A61P 25/08
See application file for complete search history.

(56) References Cited

U.S. PATENT DOCUMENTS

| | | |
|---|---|---|
| 2014/0066410 A1 | 3/2014 | Zhou et al. |
| 2016/0193206 A1 | 7/2016 | Schmees et al. |
| 2017/0360756 A1 | 12/2017 | Brown et al. |
| 2018/0092924 A1 | 4/2018 | Quinn et al. |

FOREIGN PATENT DOCUMENTS

| | | |
|---|---|---|
| CN | 103547152 A | 1/2014 |
| CN | 105229002 A | 1/2016 |
| CN | 105593224 A | 5/2016 |
| CN | 107207474 A | 9/2017 |
| CN | 109350616 A | 2/2019 |
| WO | 2017223452 A1 | 12/2017 |

OTHER PUBLICATIONS

Tojo et al., Med. Chem. Lett., publ. 2014, ACS, vol. 5, pp. 1119-1123 (Year: 2014).*
Carrette et al., PNAS, publ. Jan. 23, 2018, Nat. Acad. Sci., vol. 115(4), pp. E668-E675 (Year: 2018).*
International Search Report for PCT/CN2019/107775 dated Dec. 9, 2019, ISA/CN.
Natalie H. Theodoulou et al., Discovery of I-BRD9,a Selective Cell Active Chemical Probe for Bromodomain Containing Protein 9 inhibition, Journal of Medicinal Chemistry, Feb. 13, 2015, pp. 1425-1439.
Roberto Sanchez et al., The role of human bromodomains chromatin biology and gene transcription, NIH Public Access Author Manuscript, Sep. 2009, 12(5):1659-665.
The First Office Action of the Priority Application No. 201811548181. 6, dated Oct. 9, 2019.

* cited by examiner

*Primary Examiner* — Sarah Pihonak
(74) *Attorney, Agent, or Firm* — Yue (Robert) Xu; Apex Attorneys at Law, LLP

(57) ABSTRACT

Provided are methods of using bromodomain-containing protein 9 inhibitor (I-BRD9) or a derivative thereof in preparation of anti-epileptic drugs. The I-BRD9 has significant effects on anticonvulsion, prolonging of convulsion latency, and reduction of seizure level, and can be used for preparing anti-epileptic drug preparations.

10 Claims, 2 Drawing Sheets

USE OF I-BRD9 OR DERIVATIVES THEREOF IN PREPARING ANTI-EPILEPTIC DRUGS

CROSS REFERENCE TO RELATED APPLICATIONS

This application is a US National Phase application based upon PCT Application No. PCT/CN2019/107775 filed Sep. 25, 2019, which claims the priority of Chinese Patent Application No. 201811548181.6, filed on Dec. 18, 2018, and titled with "USE OF I-BRD9 OR DERIVATIVES THEREOF IN PREPARING ANTI-EPILEPTIC DRUGS", and the disclosures of which are hereby incorporated by reference.

FIELD

The present disclosure relates to the field of medicine, specifically to use of I-BRD9 or derivatives thereof in preparation of anti-epileptic drugs.

BACKGROUND

Epilepsy is a chronic recurrent severe neurological disease characterized by abnormal synchronized discharge of brain neurons. The occurrence of epilepsy involves changes in ion channels, synaptic remodeling, inflammation, transglial hyperplasia, and neuronal death. However, the mechanism of seizures has not been fully elucidated. Epilepsy is the second most common disease after cerebrovascular disease, and affects about 50 million patients worldwide. Among them, 20 million patients with epilepsy cannot be controlled or relieved by regular antiepileptic drug treatment, which is called refractory epilepsy. Therefore, it is particularly important to study the pathogenesis of epilepsy and find new, safer and more effective antiepileptic drugs.

The treatment of epilepsy includes drug treatment, surgical treatment, neuromodulation treatment, etc. At present, the treatment of epilepsy in China and abroad is mainly drug therapy. After a regular treatment with anti-epileptic drugs, and about 70% of patients can be controlled, wherein 50% to 60% of patients can be cured after 2 to 5 years of treatment, and patients can work and live like normal people. Therefore, reasonable and regular anti-epileptic drug treatment is the key. Although conventional anti-epileptic drugs (such as phenytoin, phenobarbital) have a certain clinical effect, they have more side effects, such as gingival hyperplasia, increased hair, high teratogenicity, hyperactivity, inattention, etc., and the patient are easily tolerated.

Through its bromodomain, the bromodomain-containing protein 9 (BRD9) can selectively recognize the acetylated lysine site of histone terminal, binds to acetylated lysine on histones, recruits transcription regulators, and assembles into transcription complexes, regulates the transcription of downstream genes, and participates in a series of important biological processes such as cell growth and immune response.

I-BRD9 (GSK602) is an effective and selective BRD9 inhibitor with a molecular weight of 497.55, a chemical formula of $C_{22}H_{22}F_3N_3O_3S_2$, a CAS number of 1714146-59-4, and a structural formula as shown in Formula I. Its $pIC_{50}$ is 7.3. For BRD4, its $pIC_{50}$ is 5.3. I-BRD9 is identified by the structural drug design method, and its selectivity is more than 700 times higher than that of the BET family, and more than 200 times higher than that of highly homologous BRD7. I-BRD9 was used in Kasumi-1 cells to identify genes related to BRD9 regulation and involved in tumor and immune response pathways.

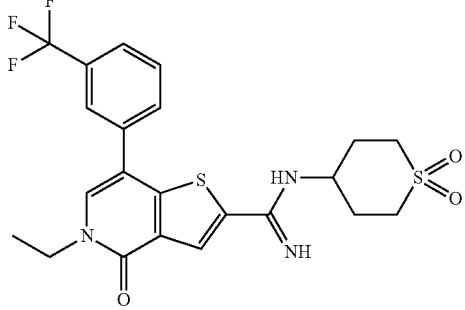

Formula I

At present, use of BRD9 inhibitor (I-BRD9) for anti-epileptic drug has not been reported.

SUMMARY

In view of above, the present disclosure provides use of I-BRD9 or derivatives thereof in preparing anti-epileptic drugs. The experiments show that bromodomain-containing protein 9 inhibitor (I-BRD9) has an obvious anti-epileptic effect.

In order to achieve the objects of the present disclosure, the present disclosure provides a following technical solution.

The present disclosure provides use of I-BRD9 or derivatives thereof in preparing anti-epileptic drugs.

Preferably, the anti-epileptic drug is administered at a dose of 1 to 100 mg/kg.

Preferably, the anti-epileptic drug is administered at a dose of 5 to 50 mg/kg.

Preferably, the anti-epileptic drug is administered at a dose of 10 to 20 mg/kg.

Preferably, the anti-epileptic drug further comprises pharmaceutically acceptable excipients.

Preferably, the anti-epileptic drug further comprises other anti-epileptic drugs.

Preferably, the anti-epileptic drug is in an injectable dosage form.

Preferably, the injectable dosage form is an injection or a powder injection.

In specific embodiments of the present disclosure, the injectable dosage form is administered by intravenous injection, intraperitoneal injection, subcutaneous injection or intramuscular injection.

Preferably, the anti-epileptic drug is administered by gastrointestinal administration.

The present disclosure provides use of I-BRD9 or derivatives thereof in preparing anti-epileptic drugs. The present disclosure has following advantages.

In the present disclosure, by observing the influence of bromodomain-containing protein 9 inhibitor (I-BRD9) upon mouse epileptic seizure induced by pentylenetetrazole, it is found that I-BRD9 has obvious effects on anticonvulsion, postponing the onset time of convulsion and reducing seizure level. The results show that the bromodomain-containing protein 9 inhibitor (I-BRD9) has an obvious anti-epileptic effect, and is suitable for preparing anti-epileptic drugs.

DETAILED DESCRIPTION

The present disclosure discloses use of I-BRD9 or derivatives thereof in preparing anti-epilepsy drugs. One of ordinary skill in the art can learn from this article and appropriately improve the process parameters to achieve. In particular, it should be noted that all similar substitutions and modifications will be obvious to one of ordinary skill in the art, and they are all considered to be included in the present disclosure. The method and application of the present disclosure have been described through preferred embodiments, and one of ordinary skill in the art can obviously modify or appropriately modify and combine the methods and applications described herein without departing from the content, spirit and scope of the present disclosure to implement and apply the technology of the present disclosure.

All the agents or instruments used in preparing anti-epileptic drugs with I-BRD9 or derivatives thereof provided in the present disclosure are purchased from the market.

The present disclosure will be described in conjunction with embodiments hereinafter.

Example 1

In the present disclosure, the animals are all 8-week-old healthy male C57BL/6 mice, weighing 22-24 grams, all purchased from Hunan SJD laboratory animal Co. LTD., license number: SCXK (Xiang) 2016-0002. C57BL/6 mice in different groups were all feed in an artificial day and night 12-hour circular lighting environment (7:00 AM-7:00 PM). The mice in the groups and were kept in cages, 4-6 mice per cage. In the cages, the mice had free access to food and water; and the daily food and water were changed regularly 60 C57BL/6 mice were randomly divided into a pentylenetetrazole model group (vehicle control group, Vehicle), an low dosage group of I-BRD9 (10 mg/kg), a medium dosage group of I-BRD9 (15 mg/kg), and a high dosage group of I-BRD9 (20 mg/kg). Animals in each group were administered with corresponding dosage of drugs or vehicle by intraperitoneal or subcutaneous injection. 1 h later, 45 mg/kg of pentylenetetrazole was intraperitoneally injected. The behaviors and conditions of the animals were observed. Later, changes of mice behaviors were closely observed through video monitoring system for 1 h, and seizure level was evaluated by Racine grading standard. The incubation period (started after the completion the administration of pentylenetetrazole, and ended by the first time muscle spasm occurred), seizure level (subjected to the highest level) and duration period of the seizure were recorded.

Seizure level of mice were referred to a modified Racine scale:

0 stage: no change;

I stage: rhythmical mouth, ears and facial twitch and spasm;

II stage: nodding and more serious facial twitch and spasm;

III stage: clonus of forelimb occurs, without up-right;

IV stage: rearing with forelimb clonus;

V stage: stiffness clonus occurs in the whole body, and falling.

Figure 1:
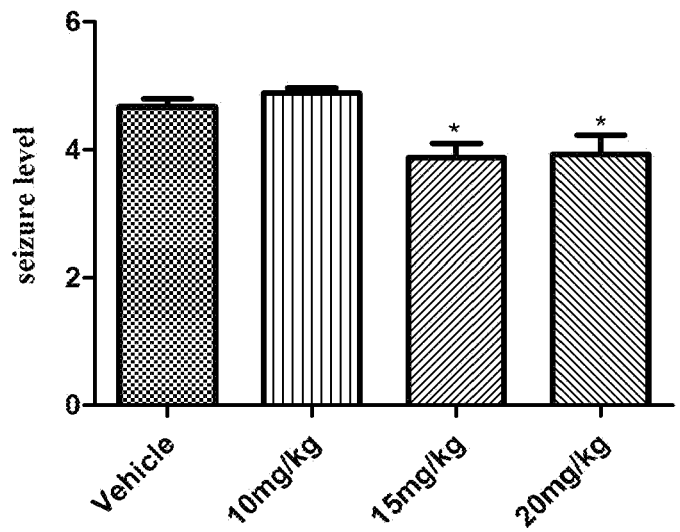
FIG. 1 shows effects of I-BRD9 on seizure level of pentylenetetrazole-induced epilepsy model mice.
Figure 2:
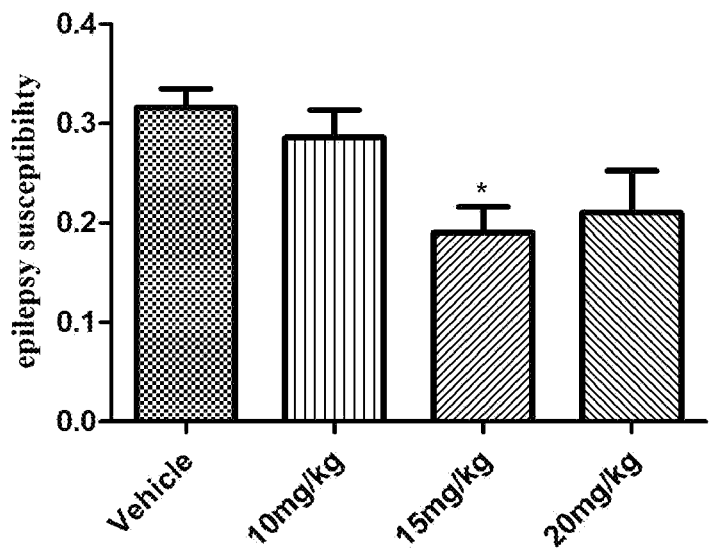
FIG. 2 shows effects of I-BRD9 on epilepsy susceptibility of pentylenetetrazole-induced epilepsy model mice.
Figure 3:
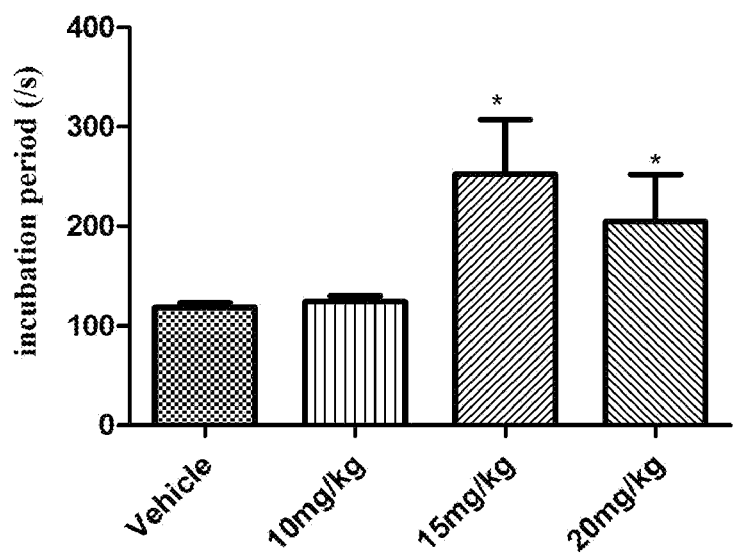
FIG. 3 shows effects of I-BRD9 on incubation period of pentylenetetrazole-induced epilepsy model mice.

The experimental results were shown in FIGS. 1 to 3. The experimental results showed that: comparing with epilepsy model group, intervene of IBRD9 obviously reduced seizure level (FIG. 1), reduced epilepsy susceptibility (FIG. 2), and postpone the onset time of epilepsy (FIG. 3), indicating that IBRD9 has improving effects on pentylenetetrazole-induced epilepsy.

The above descriptions are only preferred embodiments of the present disclosure. It should be noted that a number of modifications and refinements may be made by one of ordinary skills in the art without departing from the principles of the disclosure, and such modifications and refinements are also considered to be within the scope of protection of the disclosure.

What is claimed is:

1. A method for treating epilepsy, comprising administering I-BRD9 to a subject in need thereof.

2. The method according to claim 1, wherein the I-BRD9 is administered at a dose of 1 to 100 mg/kg.

3. The method according to claim 1, wherein the I-BRD9 is administered at a dose of 5 to 50 mg/kg.

4. The method according to claim 1, wherein the I-BRD9 is administered at a dose of 10 to 20 mg/kg.

5. The method according to claim 1, wherein the I-BRD9 is in a form of composition which further comprises pharmaceutically acceptable excipients.

6. The method according to claim 1, further comprising administering to the subject in need thereof other anti-epileptic drugs.

7. The method according to claim 1, wherein the I-BRD9 is in an injectable dosage form.

8. The method according to claim 7, wherein the injectable dosage form is an injection or a powder-injection.

9. The method according to claim 7, wherein the injectable dosage form is administered by intravenous injection, intraperitoneal injection, subcutaneous injection or intramuscular injection.

10. The method according to claim 1, wherein the I-BRD9 is administered by gastrointestinal administration.

* * * * *